(12) United States Patent
Chang

(10) Patent No.: US 6,369,964 B1
(45) Date of Patent: Apr. 9, 2002

(54) OPTICAL FILTERS FOR REDUCING EYE STRAIN, DURING SURGERY

(75) Inventor: Byung Jin Chang, Ann Arbor, MI (US)

(73) Assignee: General Scientific Corporation, Ann Arbor, MI (US)

(*) Notice: Subject to any disclaimer, the term of this patent is extended or adjusted under 35 U.S.C. 154(b) by 0 days.

(21) Appl. No.: 09/148,289

(22) Filed: Sep. 4, 1998

(51) Int. Cl.⁷ .............................. G02B 5/22; A61B 1/06
(52) U.S. Cl. .................... 359/885; 359/892; 600/181
(58) Field of Search ........................... 359/885, 892; 396/14, 17; 600/181

(56) References Cited

U.S. PATENT DOCUMENTS

| | | | |
|---|---|---|---|
| 3,445,153 A | 5/1969 | Marks et al. | 350/144 |
| 3,704,928 A | 12/1972 | Coombs et al. | 350/1 |
| 4,170,987 A | 10/1979 | Anselmo et al. | 128/665 |
| 4,188,095 A | 2/1980 | Holladay | 351/36 |
| 4,320,939 A * | 3/1982 | Mueller | 359/885 |
| 4,602,856 A | 7/1986 | Marks | 351/44 |
| 4,685,451 A * | 8/1987 | Ando | 348/70 |
| 4,848,897 A * | 7/1989 | Aizu et al. | 351/221 |
| 4,962,425 A | 10/1990 | Rea | 358/139 |
| 4,976,524 A * | 12/1990 | Chiba | 359/708 |
| 5,009,655 A | 4/1991 | Daignault, Jr. et al. | 606/7 |
| 5,057,744 A | 10/1991 | Barbier et al. | 315/10 |
| 5,151,821 A | 9/1992 | Marks | 359/462 |
| 5,155,776 A | 10/1992 | Concannon et al. | 382/7 |
| 5,243,460 A * | 9/1993 | Kornberg | 351/162 |
| 5,313,070 A | 5/1994 | Vala et al. | 250/571 |
| 5,367,386 A | 11/1994 | Copenhaver et al. | 358/474 |
| 5,388,987 A | 2/1995 | Badoz et al. | 433/29 |
| 5,400,174 A * | 3/1995 | Pagis et al. | 359/589 |
| 5,408,085 A | 4/1995 | Vala et al. | 250/208 |
| 5,422,474 A | 6/1995 | Vala et al. | 250/208.1 |
| 5,426,662 A | 6/1995 | Mefferd et al. | 372/99 |
| 5,434,419 A | 7/1995 | Decupper | 250/372 |
| 5,479,293 A | 12/1995 | Reed | 359/432 |
| 5,489,274 A | 2/1996 | Chu et al. | 604/167 |
| 5,513,274 A | 4/1996 | Concannon et al. | 382/138 |
| 5,530,784 A | 6/1996 | Copenhaver et al. | 385/119 |
| 5,701,361 A | 12/1997 | Concannon et al. | 382/138 |
| 5,707,401 A * | 1/1998 | Talmore | 607/88 |
| 5,717,779 A | 2/1998 | Concannon et al. | 382/135 |
| 5,725,970 A * | 3/1998 | Martin et al. | 359/3 |
| 5,731,894 A * | 3/1998 | Gross | 359/371 |
| 5,734,693 A | 3/1998 | Quint et al. | 378/185 |
| 5,773,172 A * | 6/1998 | Karasawa et al. | 359/885 |
| 5,828,437 A * | 10/1998 | Hubert-Habart et al. | 351/44 |
| 6,021,344 A * | 2/2000 | Lui et al. | 600/476 |

* cited by examiner

Primary Examiner—Cassandra Spyrou
Assistant Examiner—Jennifer Winstedt
(74) Attorney, Agent, or Firm—Gifford, Krass, Groh, Sprinkle, Anderson & Citkowski, PC

(57) ABSTRACT

Viewing apparatus, for medical and surgical practitioners incorporating one or more optical filters, each exhibiting a reverse photopic response, such that green light is at least partially attenuated, whereas red and blue light are both substantially transmitted. The invention includes means for supporting one or more optical filters in the practitioner's field of view, such as a pair of eyeglass frames or endoscope mounting for use, for example, in conjunction with laparoscopic surgery. Various technologies may be employed to realize a desired reverse photopic response, including absorptive dyes, dielectric layers, and/or holograms.

9 Claims, 6 Drawing Sheets

OPTICAL FILTERS FOR REDUCING EYE STRAIN, DURING SURGERY

FIELD OF THE INVENTION

The present invention relates generally to optical filtering and, in particular, to a filter exhibiting a reverse photopic response, and means for supporting such filters for use during prolonged surgical and diagnostic procedures, in particular.

BACKGROUND OF THE INVENTION

The human eye has two classes of receptors: cones and rods. These are located on the innermost membrane of the eye, called the retina, on which objects are imaged. The cones in each eye number between six and seven million. They are located primarily in the central portion of the retina called the fovea, and are highly sensitive to color. Humans can resolve fine details with these cones largely because each one is connected to its own nerve end. Cone vision is known as photopic or bright-light vision.

The number of rods is much larger, on the order of 75 to 100 million, and are distributed over the retinal surface. The larger area of distribution and the fact that several rods are connected to a single nerve end reduces the amount of detail discernible by the receptors. Rods serve to provide a general, overall picture of the field of view. They are not involved in color vision, but are sensitive to low level of illumination. In dim light only the rods are stimulated and objects appear colorless. This characteristic is known as scotopic vision.

As a result of extensive tests with hundreds of observers, the primary colors have been standardized by the Commission International d'Eclairage (CIE) based on the principle of color matching in colorimetry. The CIE primaries are: red (700 nm), green (546.1 nm), and blue (435.8 nm). These primaries produce the maximum response to the eye compared to other wavelengths.

Color vision depends greatly on the illumination. Colors are better resolved in a brightly illuminated scene. Certain colors will produce a higher sensation of brightness than others. This is indicated in FIG. 1, which shows the relative luminosity curve for spectral colors radiated at a constant energy level. As can be from this figure, the human eye is most sensitive to green at about a 555-nm wavelength.

However, the dominant colors associated with most surgical observations are red, blue, and yellow. A limited number of internal organs incorporate the color green. As a consequence, due to the fact that human eyes are most sensitive over a spectral range of 525 nm to 575 nm, in many surgical and diagnostic/examination procedures, physicians must resort to very bright illumination to visualize details. This use of bright light increases eye strain in conjunction with such prolonged procedures. Clearly any advance which would allow a lesser degree of illumination or reduce the attendant eye strain would be welcome by the medical/surgical community, in particular.

SUMMARY OF THE INVENTION

The present invention resides in viewing apparatus, particularly for medical and surgical practitioners. Broadly, and in general terms, the invention provides an optical filter incorporating means for achieving a reverse photopic response, such that green light is at least partially attenuated, whereas red and blue light are both substantially transmitted. Since, in the human body, internal organs, blood vessels, and so forth, are primarily red or blue as opposed to green, a practitioner viewing a patient through such a filter may do so using a reduced level of illumination, thereby alleviating eye strain and increasing image contrast. That is, by virtue of the invention, with one or more shade of green removed or attenuated from a medical view containing mostly red and/or blue, either the red colors, the blue colors, or both, become more pure, thereby increasing the contrast therebetween.

The invention includes means for supporting one or more optical filters in the practitioner's field of view, each filter exhibiting a reverse photopic response. In one embodiment, the means for supporting the filters includes a pair of eyeglass frames, whereas, in an alternative embodiment, the means for supporting the filters forms part of an endoscope for use, for example, in conjunction with laparoscopic surgery. Various technologies may be employed to realize a desired reverse photopic response, including absorptive dyes, dielectric layers, and/or holograms.

DETAILED DESCRIPTION OF THE INVENTION

Figure 2:
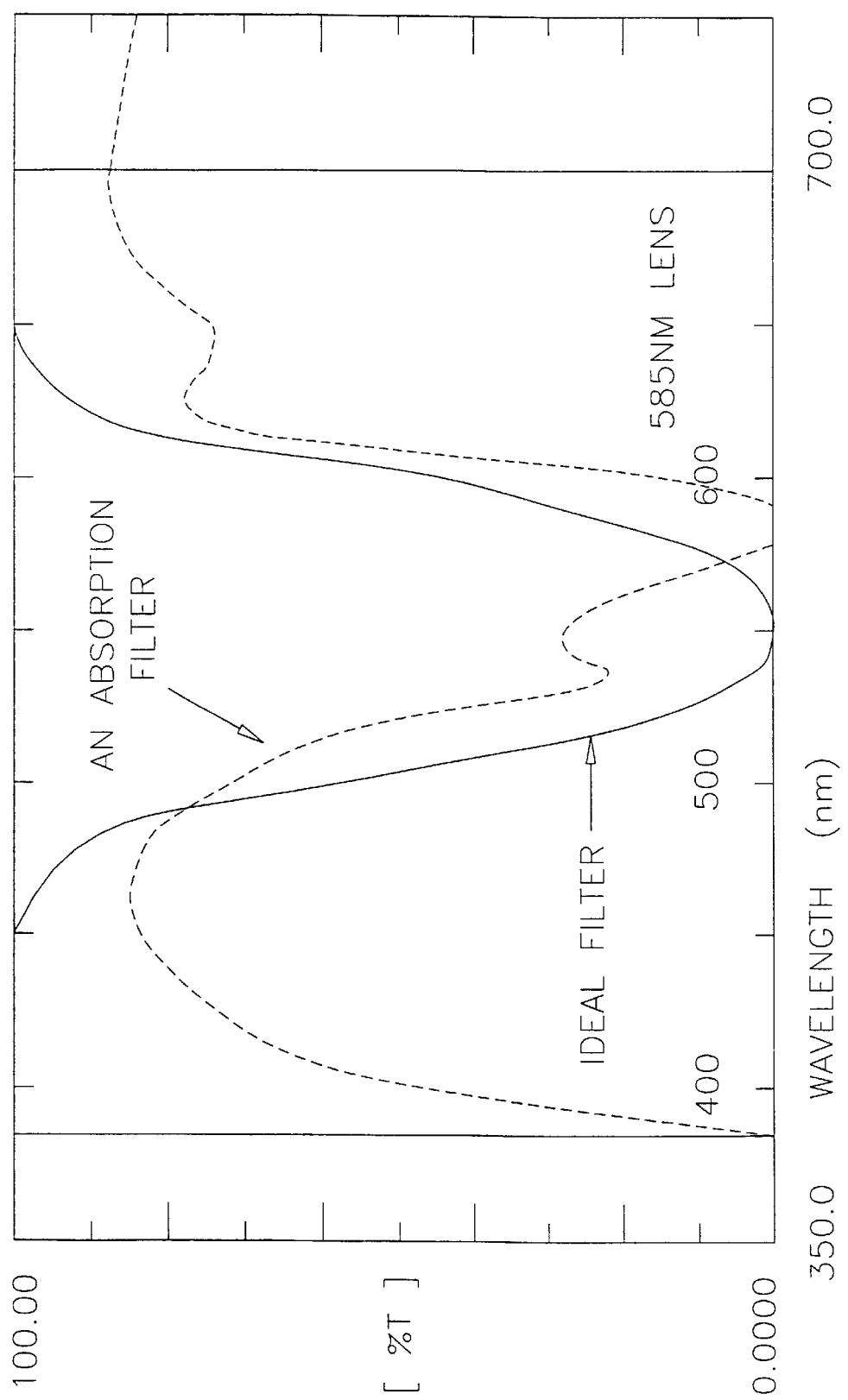
FIG. 2 illustrates two curves, one for an ideal reverse-photopic filter according to the invention, and another for an absorption filter which approximates the ideal response.

The present invention reduces the eye strain experienced by medical and surgical practitioners, in particular, by reducing intensities of wavelengths that are not critical for surgical and diagnostic procedures. FIG. 2 is a graph which illustrates an ideal filter curve (solid line) and a curve exhibited by one physical realization of a filter utilizing absorption dyes (broken line). Broadly, the invention provides a filter featuring what will be termed herein as an "inverse photopic response," in that wavelengths in the green part of the spectrum are at least partially attenuated, whereas wavelengths outside of this range, in the red and blue, and yellow, are substantially transmitted. Utilizing such an approach, for a given degree of illumination, by blocking out green wavelengths which are substantially non-critical for surgical and diagnostic procedures, a practitioner using one or more filters according to the invention will be able to nevertheless perceive adequate detail without receiving unnecessary optical energy in the green range.

Figure 1:
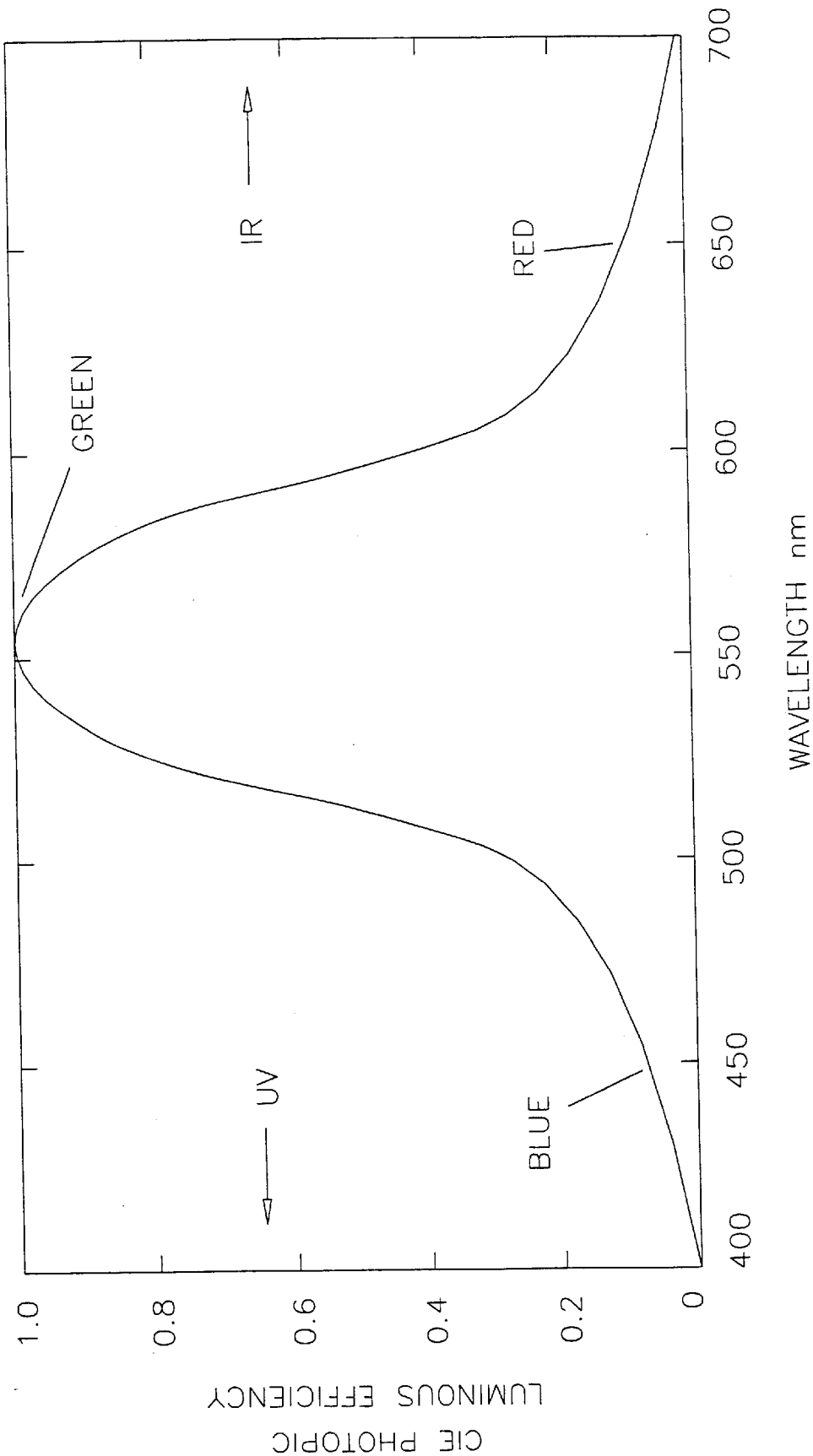
FIG. 1 is a curve plotting CIE photopic luminous efficiency versus wavelength.

Continuing the reference to FIG. 2, an "ideal" filter according to the invention would exhibit an optical response representative of a smooth curve embodying a mirror image of the curve of FIG. 1, in that, in the range of about 500–600 nm, wavelengths would become substantially attenuated and completely blocked around the peak energy of 550 nm. At the same time, outside of this range, namely, at wavelengths less than about 450 nm and in excess of 650 nm, substantially complete transmission would take place.

So far, we have realized an absorption filter exhibiting the characteristics illustrated by the broken line of FIG. 2. In particular, through the use of a dielectric stack having a plurality of layers combining high and low index, we have been able to achieve a response that tracks the ideal filter, in that transmission around 450 nm and above about 625 nm is substantial, whereas, in the range of 500–600 nm in particular, a high degree of attenuation takes place, with complete blockage occurring in a range of about 575–590 nm. More specifically, in a preferred embodiment, a dielectric stack includes 30 layers to achieve such a characteristic, though more or fewer such layers may be incorporated, depending upon the performance desired. Although the response characteristic illustrated by this curve is not ideal, in that transmission never reaches 100 percent and the peak attenuation is not centered at 550 nm, the results are quite usable in medical and surgical applications to which the invention is primarily directed.

It will be apparent to one of skill in the art of optical element design that technologies other than absorption dyes may be used to produce a filter having an inverse photopic response suitable for use in applications prescribed by the invention. In particular, the skilled practitioner would realize that a stack of dielectric or dichroic filters may alternatively be utilized to obtain a desired response, and that holographic techniques may be used as well. The choice of a particular technology is subject only to the exactitude of optical response desired and trade-offs involving cost, manufacturing and devise longevity.

Figure 3:
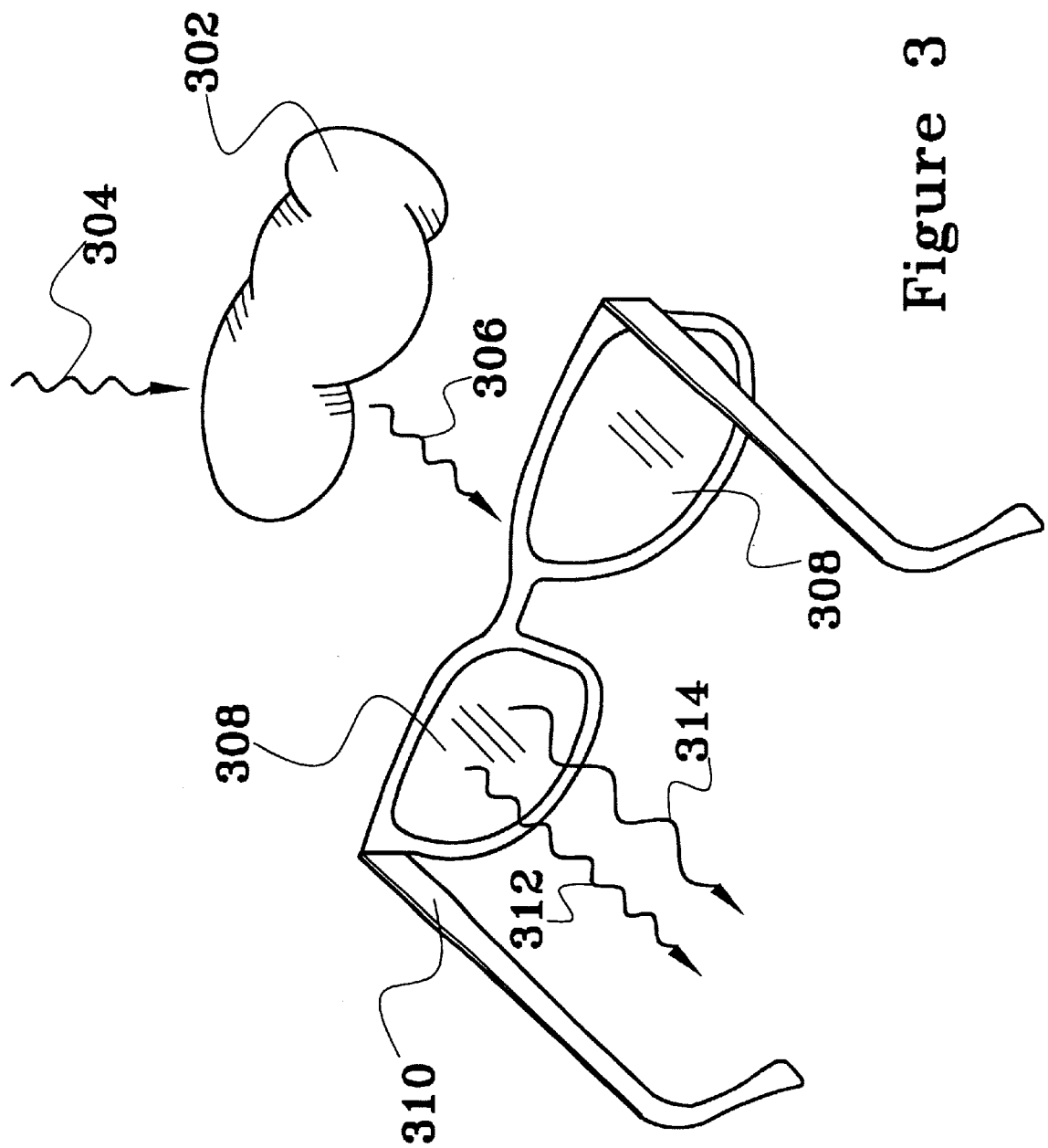
FIG. 3 illustrates a physical realization of the invention wherein reverse-photopic filters are incorporated into a pair of eyeglass frames.
Figure 4:
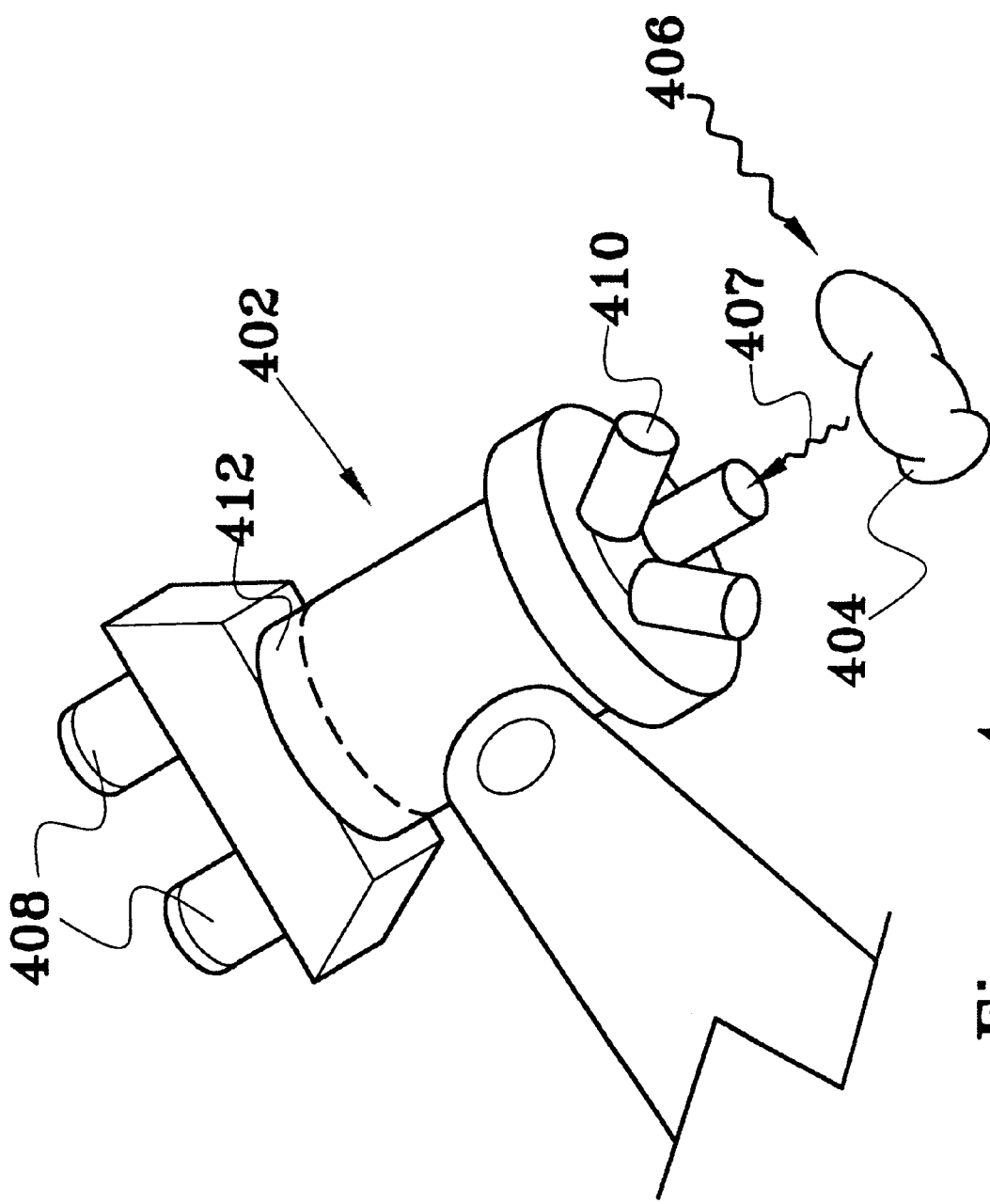
FIG. 4 illustrates an alternative configuration according to the invention wherein reverse-photopic filters are incorporated into a microscope.
Figure 5:
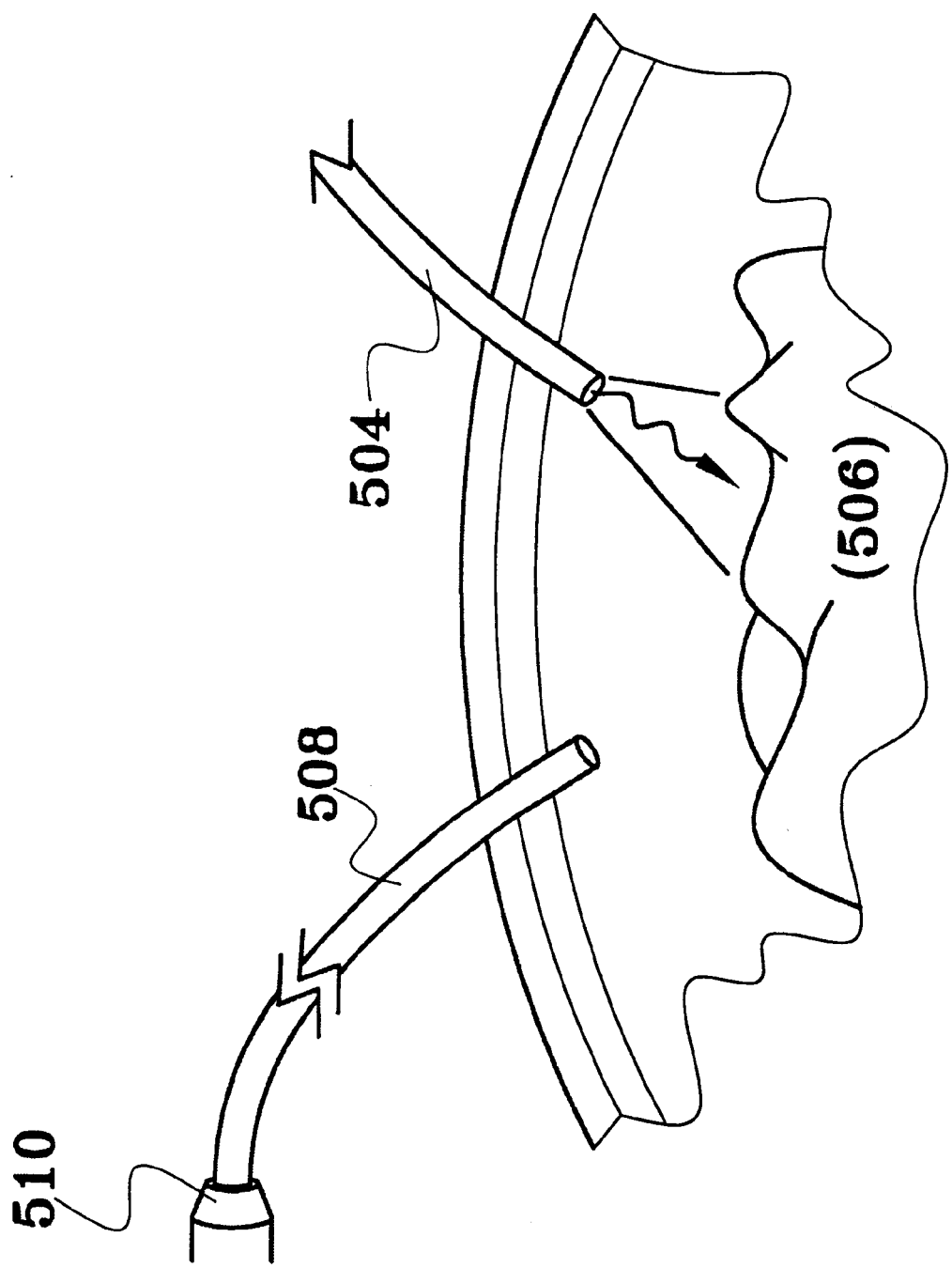
FIG. 5 illustrates yet a further embodiment of the invention wherein a reverse-photopic filter is incorporated into an endoscope for use, for example, in conjunction with arthroscopic surgery.

Now making reference to FIGS. 3–5, the invention is applicable to various viewing situations, including situations outside of the medical/surgical profession, with the only requirement being the desire to obtain a reverse photopic response as disclosed herein. FIG. 3 illustrates a primary embodiment of the invention wherein an internal body organ 302 is illuminated with light 304, resulting in reflected wavelengths 306 potentially incorporating a broad spectrum of high-intensity radiation. Use of filters 308 in eyeglass frames 310, permit passage of shorter wavelengths 312 of the type associated with blue and violet, and longer wavelengths such as 314 of the type associated with red and yellow, while effectively blocking wavelengths in the green range, thereby reducing eye strain and increasing image contrast.

In FIG. 4, illustrated generally at 402, is an alternative use of the invention in a microscope application, used to view an object 404 illuminated with radiation 406. Again, the reflected radiation 407 may include a broad range of high-intensity wavelengths, but through the use of reverse-photopic filters 408, only wavelengths of interest in the red/blue and/or yellow regions are passed to the practitioner. It should be noted that in lieu of using two filters 408 at the eye pieces, a single filter may be used in conjunction with the objective 410, and may be incorporated into the body of the instrument as depicted by the element 412 shown in broken-line form.

FIG. 5 illustrates yet a further alternative implementation of the invention, in this case, a filter 510 incorporated onto an endoscope 508, used to observe an internal organ 506 illuminated by a source of light 504, typically in the form of an optical fiber bundle. The use of endoscopes, and the like, are becoming increasingly popular with arthroscopic surgery, for example. Of course, if the endoscope 508 is coupled to a video camera, the need for a filter 510 would be obviated, since the practitioner would be viewing a video monitor as opposed to direct viewing.

Figure 6:
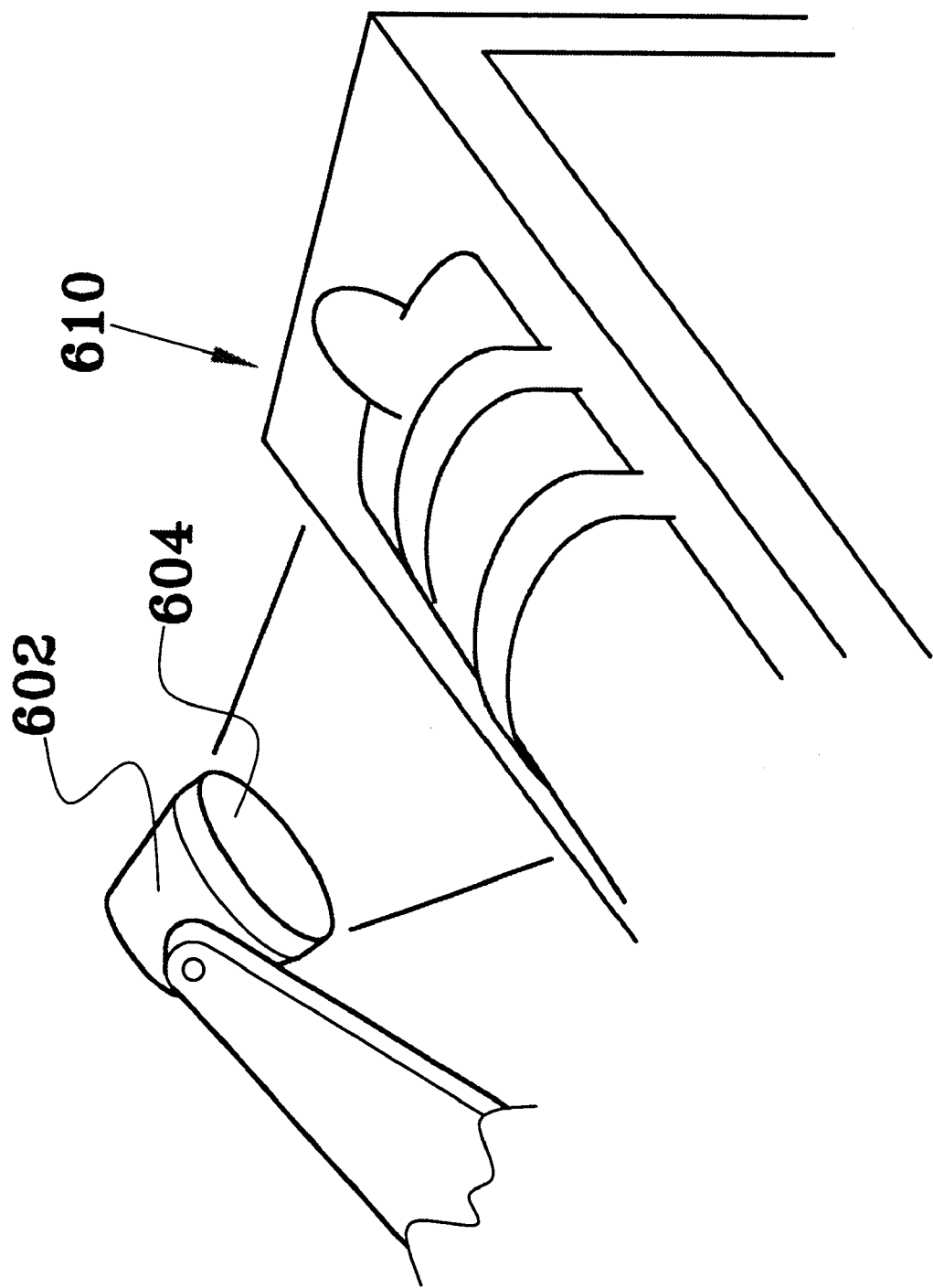
FIG. 6 illustrates the way in which a filter may be adapted to a source of illumination as opposed to reflection-light reception.

FIG. 6 illustrates yet a further alternative embodiment of the invention, wherein a filter 604 according to the teachings contained herein is associated with a source of 602 as opposed to the receipt of reflected light, in this case, the high-intensity lamp of the type used in a surgical suite to illuminate a patient 610, for example, on an operating table.

I claim:

1. Viewing apparatus for a surgical practitioner having a field of view of a patient's internal organs, the apparatus comprising:
   a pair of filters exhibiting a reverse photopic response, in that light substantially in the green portion of the spectrum is at least partially attenuated, whereas red and blue light are both substantially transmitted; and
   a support structure for holding the filter in the field of view of the practitioner, the support structure being in the form of an eyeglass frame adapted to be worn by the surgical practitioner;
   whereby the attenuation of the green light reduces eye strain while enhancing the contrast of the patient's internal organs.

2. The viewing apparatus of claim 1, wherein one or more absorptive dyes are used in the filters to achieve the reverse photopic response.

3. The viewing apparatus of claim 1, wherein one or more dielectric layers are used in the filters to achieve the reverse photopic response.

4. The viewing apparatus of claim 1, wherein one or more holograms are used in the filters to achieve the reverse photopic response.

5. Viewing apparatus for a surgical practitioner having a field of view of a patient's internal organs, the apparatus comprising:
   a filter exhibiting a reverse photopic response, in that light substantially in the green portion of the spectrum is at least partially attenuated, whereas red and blue light are both substantially transmitted; and
   a support structure for holding the filter in the field of view of the practitioner, wherein the support structure forms part of an endoscope;
   whereby the attenuation of the green light reduces eye strain while enhancing the contrast of the patient's internal organs.

6. A method of improving visibility at a reduced level of illumination with respect to a surgical operation on a patient having internal organs, comprising the steps of:
   exposing one or more of the patient's internal organs;
   illuminating the internal organs with substantially white light; and
   observing the illuminated organs through an optical filter exhibiting a reverse photopic response, in that light substantially in the green portion of the spectrum is at least partially attenuated, whereas red and blue light are both substantially transmitted.

7. The method of claim 6, wherein the step of observing the illuminated organs through an optical filter exhibiting a reverse photopic response includes the step of observing the organs through a pair of filters supported in a pair of eyeglass frames worn by a user.

8. The method of claim 6, wherein the step of observing the illuminated organs through an optical filter exhibiting a reverse photopic response includes the step of observing the organs through an endoscope incorporating the filter.

9. The method of claim 6, wherein the step of observing the illuminated organs through an optical filter exhibiting a reverse photopic response includes the step of observing the organs through a microscope incorporating the filter.

* * * * *